(12) United States Patent
Barrera et al.

(10) Patent No.: US 12,636,087 B2
(45) Date of Patent: May 26, 2026

(54) SYSTEMS AND METHODS FOR ENHANCING IMAGING DURING SURGICAL PROCEDURES

(71) Applicant: Covidien LP, Mansfield, MA (US)

(72) Inventors: Osvaldo A. Barrera, Madison, CT (US); Joe D. Sartor, Longmont, CO (US); David N. Heard, Boulder, CO (US)

(73) Assignee: Covidien LP, Mansfield, MA (US)

( * ) Notice: Subject to any disclaimer, the term of this patent is extended or adjusted under 35 U.S.C. 154(b) by 248 days.

(21) Appl. No.: 18/008,504

(22) PCT Filed: May 7, 2021

(86) PCT No.: PCT/US2021/031318
§ 371 (c)(1),
(2) Date: Dec. 6, 2022

(87) PCT Pub. No.: WO2022/026027
PCT Pub. Date: Feb. 3, 2022

(65) Prior Publication Data
US 2023/0210603 A1     Jul. 6, 2023

Related U.S. Application Data

(60) Provisional application No. 63/058,837, filed on Jul. 30, 2020.

(51) Int. Cl.
A61B 34/20 (2016.01)
A61B 8/14 (2006.01)

(52) U.S. Cl.
CPC .............. A61B 34/20 (2016.02); A61B 8/14 (2013.01); A61B 2034/2055 (2016.02)

(58) Field of Classification Search
None
See application file for complete search history.

(56) References Cited

U.S. PATENT DOCUMENTS 9,675,319 B1     6/2017   Razzaque et al.
2009/0275937 A1*  11/2009  Stokes .............. A61B 18/1492
606/33

(Continued)

FOREIGN PATENT DOCUMENTS

WO     2013176857 A1   11/2013

OTHER PUBLICATIONS

International Search Report and Written Opinion of the International Searching Authority issued in corresponding application PCT/US2021/031318 mailed Aug. 16, 2021 (16 pages).

(Continued)

*Primary Examiner* — Michael J Carey
*Assistant Examiner* — Marjan Saboktakin
(74) *Attorney, Agent, or Firm* — Carter, DeLuca & Farrell, LLP

(57) ABSTRACT

A surgical system is configured to augment the visualization environment presented to the surgeon by merging, in real-time, video feed and ultrasound imaging; tracking anatomy and instruments; identifying critical structures; generating and displaying 3-dimensional models of relevant anatomy; providing actionable guidance to the user; and enabling data collection and processing. The surgical system may include a tissue-marking surgical instrument configured to simultaneously identify critical structures beneath an organ surface and mark the organ surface at a location overlapping the identified critical structures.

12 Claims, 9 Drawing Sheets

20

(56)           References Cited

U.S. PATENT DOCUMENTS

| | | | |
|---|---|---|---|
| 2010/0168561 A1 | 7/2010 | Anderson | |
| 2012/0109151 A1 | 5/2012 | Maier-Hein | |
| 2013/0274596 A1 | 10/2013 | Azizian | |
| 2013/0317352 A1* | 11/2013 | Case | A61B 90/04 |
| | | | 382/128 |
| 2014/0005542 A1 | 1/2014 | Bizzell et al. | |
| 2016/0120607 A1* | 5/2016 | Sorotzkin | A61B 8/4444 |
| | | | 600/441 |
| 2017/0360395 A1* | 12/2017 | Razzaque | A61B 6/487 |
| 2019/0216574 A1 | 7/2019 | Coleman et al. | |
| 2021/0196425 A1* | 7/2021 | Shelton, IV | G16H 40/63 |

OTHER PUBLICATIONS

Examination Report issued in corresponding application EP 21733247.7 dated Apr. 8, 2025 (5 pages).
Office Action issued in corresponding Chinese Application No. 202180058343.1, together with the English language translation obtained from the Global Dossier.

* cited by examiner 102    104

20

"M"

"M"

20          109

SYSTEMS AND METHODS FOR ENHANCING IMAGING DURING SURGICAL PROCEDURES

CROSS-REFERENCE TO RELATED APPLICATION

This application is a U.S. National Stage Application filed under 35 U.S.C. § 371 (a) of International Patent Application No. PCT/US2021/031318, filed on May 7, 2021, which claims the benefit of the filing date of provisional U.S. Patent Application No. 63/058,837, filed on Jul. 30, 2020.

FIELD

The present disclosure relates to devices, systems, and methods for enhancing imaging during surgical procedures, and more particularly, to real-time enhancement of images of a surgical site for guiding surgical procedures.

BACKGROUND

Robotic surgical systems and laparoscopic surgery systems are used to perform minimally invasive surgical procedures that offer many benefits over traditional open surgery techniques, including less pain, shorter hospital stays, quicker return to normal activities, minimal scarring, reduced recovery time, and less injury to tissue. Surgical systems may include an image capturing device to allow a clinician to view the surgical site in real-time.

Ultrasound provides views of tissue structures inside the body and organs. Ultrasound systems provide many specialized image modalities including doppler for identifying flow in vessels and elastography, defines tissue based on movement of local or larger tissue regions. The image provided by ultrasound is difficult for untrained users to interpret as structures within the body and medical use often requires an ultrasound certification.

SUMMARY

The disclosure relates to devices, systems, and methods for providing intraoperative images of a surgical operative site and for guiding a surgical procedure. The system includes an imaging device configured to acquire images of the surgical operative site, a laparoscopic or robotic ultrasound probe configured to acquire images of structures at the surgical operative site, and a display configured to display, in real-time, the images of the surgical operative site, and superimpose an augmented image of the structures over the displayed images of the surgical operative site.

In accordance with another aspect of the disclosure, a method for imaging a surgical site is provided and includes receiving images of a surgical operative site; receiving ultrasound images of structures within the surgical operative site; displaying, in real-time, the received images of the surgical operative site; and superimposing an augmented image of the structures over the displayed images of the surgical operative site based on optical positioning of the ultrasound probe, and the white light camera.

In aspects, the system may be configured to continue to orient and display information acquired from the ultrasound probe after the ultrasound probe is removed from the surgical field using either organ structure, marks, or applied fiducials on the tissue to orient such images.

In accordance with another aspect of the disclosure, a method for preparing a surgical site for a surgical procedure is provided and includes: positioning a surgical instrument over an organ; imaging the organ with the surgical instrument; identifying a critical structure beneath a surface of the organ based on the imaging; and marking the surface of the organ at a location overlapping with the identified critical structure of the organ.

In aspects, the surface of the organ may be marked with the same surgical instrument used to image the organ.

In aspects, marking the surface of the organ may include marking the surface of the organ with a mark having a shape and size that approximates a shape and size of the identified critical structure.

In aspects, the critical structure may include a tumor and/or a blood vessel.

In aspects, marking the surface of the organ may include applying energy to the surface of the organ sufficient to burn the surface of the organ.

In aspects, marking the surface of the organ may include applying an ink, dye, or chemical agent to the surface of the organ.

In aspects, the method may further include: receiving an image of the surface of the organ; receiving ultrasound images of the underlying structure; displaying, in real-time, the received image of the surface of the organ; and superimposing an augmented image of the critical structure over the displayed image of the surface of the organ.

In accordance with another aspect of the disclosure, a tissue-marking device is provided and includes an outer housing portion, a marking element supported in the outer housing portion and configured to mark a surface of an organ, and an image sensor assembly supported in the outer housing portion and configured to locate an underlying structure of the organ.

In aspects, the marking element may include a heating element configured to apply energy to the surface of the organ.

In aspects, the marking element may include an applicator configured to apply an ink, dye, or chemical agent to the surface of the organ.

In aspects, the image sensor assembly may include an ultrasound transducer.

In aspects, the ultrasound transducer may be configured to generate an image of the underlying structure.

In aspects, the tissue-marking device may further include a processor in communication with the marking element and the image sensor assembly. The processor may be configured to automatically actuate the marking element to mark the surface of the organ upon the image sensor assembly locating the underlying structure.

In accordance with another aspect of the disclosure, a surgical system is provided and includes an imaging device configured to acquire an image of an organ, a surgical instrument configured to locate an underlying structure within the organ, and a display configured to display, in real-time, the image of the organ; and superimpose an augmented image of the underlying structure over the displayed image of the organ.

In aspects, the surgical instrument may include a marking element configured to mark a surface of the organ, and an image sensor assembly configured to locate the underlying structure of the organ.

In aspects, the surgical system may further include a processor in communication with the marking element and the image sensor assembly. The processor may be configured to automatically actuate the marking element to mark the surface of the organ upon the image sensor assembly locating the underlying structure.

Further details and aspects of various embodiments of the disclosure are described in more detail below with reference to the appended figures.

BRIEF DESCRIPTION OF THE DRAWINGS

Embodiments of the disclosure are described herein with reference to the accompanying drawings, wherein.

Figure 1:
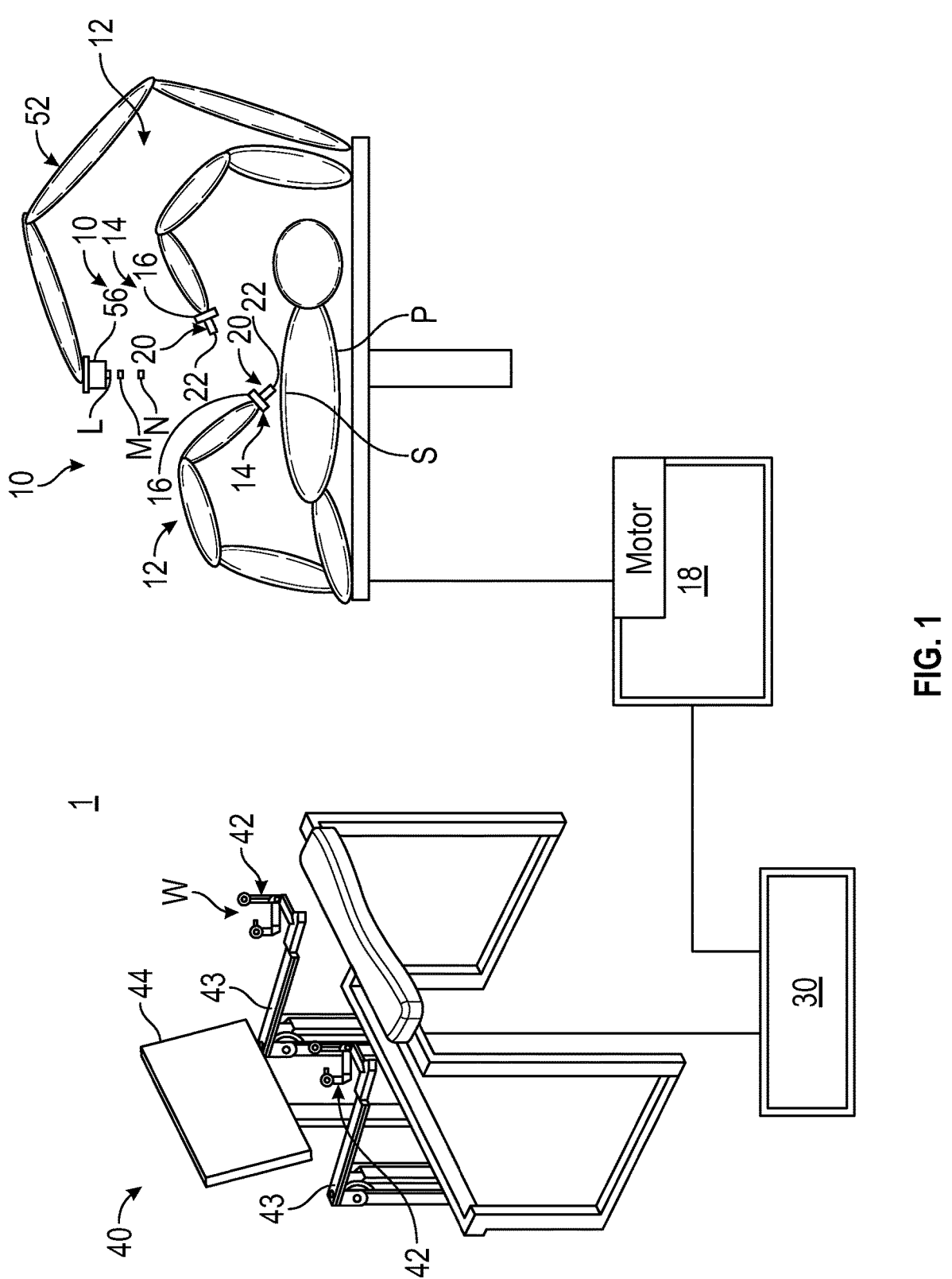
FIG. 1 is a schematic illustration of a user interface and a robotic system in accordance with the present disclosure.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is closer to a surgical site, while the term "proximal" refers to that portion of a structure that is further from the surgical site. The term "clinician" refers to a doctor, nurse, or other care provider and may include support personnel.

Laparoscopic and robotic surgery camera systems only allow surgeons to visualize the surface of the organs in the field of view, but not the underlying structures (e.g. vessels, tumors, etc.). Other technologies like ultrasound provide visualization of deeper structures, but ultrasound systems are not optimized for what surgeons need in the operating room. For example, images generated by ultrasound imaging are typically dissociated from the surgeons' tasks and appear better suited for diagnostics purposes than for real time visualization during surgery.

A system is needed that reduces the complexity of ultrasound use and integrates it into the optical systems familiar to surgeons. The system preserves the useful surgical information from the ultrasound, extending the temporal utility of that information after the ultrasound is removed.

The present disclosure provides surgical systems configured to augment the visualization environment presented to the surgeon by merging, in real-time, video feed and ultrasound imaging; tracking anatomy and instruments; identifying critical structures; generating and displaying 3-dimensional models of relevant anatomy; providing actionable guidance to the user; and enabling data collection and processing. Moreover, the disclosed system integrates connectivity with medical devices such as energy-based surgical devices and surgical stapling devices. More specifically, the system integrates video and ultrasound imaging, as well as tracking information of multiple surgical devices, to provide surgeons with an augmented reality environment for robotic and laparoscopic surgery. The disclosed system enhances surgical visualization; implements critical structure detection; provides anatomy 3D reconstruction and projections; delivers actionable guidance to optimize surgery flow, patient safety, and outcomes; improves surgical instrument control; and generates thorough documentation and data analysis. The system conveys the above-noted information to the clinician using visual and/or audible cues including suggesting procedure steps and the most suitable instrument path. When implemented in a robotic surgical system or with actuated instruments, the system is configured to drive the instruments and/or cameras. In some aspects, the system may be configured to capture and correlate data from multiple sources and medical devices simultaneously, which may be used in data analytic scenarios, procedures, and device optimization.

Another aspect of the disclosure is directed to a computer unit configured to process both ultrasound and optical images. The complexity of optical imaging has led to extensive need for powerful graphic computation engines, graphics processing units ("GPU") being the most preferred. Ultrasound has gained improvement by elimination of dedicated electronics in favor of software based image processing preferably executed by a GPU or other advanced graphics processor. By simultaneously processing both optics pipelines and ultrasound pipelines in a single GPU, the images are inherently better combined in real time while the hospital system benefits by reduced hardware expense and clutter within the OR.

Referring to FIG. 1, a robotic surgical system 1 in accordance with the present disclosure is shown generally as a robotic system 10, a processing unit 30, and a user interface 40. The robotic system 10 generally includes linkages or arms 12 and a robot base 18. In aspects, the system 1 may be a manually-operated laparoscopic surgical system rather than a robotic system. The arms 12 movably support a tool 20 having an end effector 22, which is configured to act on tissue. The end effector 22 may be a bipolar instrument, a monopolar instrument, an ablation instrument, a thermal treatment instrument, an ultrasonic instrument, a tissue grasper, a surgical stapler, a microwave instrument, or a radiofrequency instrument. It is contemplated that the robotic surgical system 1 may include a surgical instrument separate from the robot arms 12 for manual control by a clinician.

The arms 12 each have an end 14 that supports tool 20. In addition or alternatively, the ends 14 of the arms 12 may include an imaging device 16 for imaging a surgical site "S." The imaging device 16 may be a camera, a laparoscopic ultrasound probe, an endoscope, or any other suitable intra-operative imaging device. The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S," an imaging device positioned adjacent the patient, imaging device 56 positioned at a distal end of an imaging linkage or arm 52). The imaging devices (e.g., imaging devices 16, 56) may capture visual images, infra-red images, ultrasound images, X-ray images, thermal images, and/or any other known real-time images of the surgical site "S." The imaging devices transmit captured imaging data to the processing unit 30, which may create three-dimensional images of the surgical site "S" in real-time from the imaging data and transmits the three-dimensional images to the display device 44 for display. In aspects, the images of the surgical site "S" may be a real-time video feed of the surgical site. It is contemplated that imaging device 56 may be an optical trocar or the like capable of capturing 2D/3D images in the visible spectrum of light, in the infrared spectrum, or in any other spectrum contemplated, as well as to be able to apply filtering and processing thereto to enhance the images/videos captured.

The user interface 40 may include input handles 42 which are supported on control arms 43, which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include input devices (not shown) which allow the surgeon to manipulate (e.g., clamp, grasp, fire, open, close, rotate, thrust, slice, etc.) the end effectors 22 of the tools 20 supported at the ends 14 of the arms 12.

For a detailed discussion of the construction and operation of a robotic surgical system 1, reference may be made to U.S. Pat. No. 8,828,023, the entire contents of which are incorporated herein by reference.

Figures 2A, 2B:
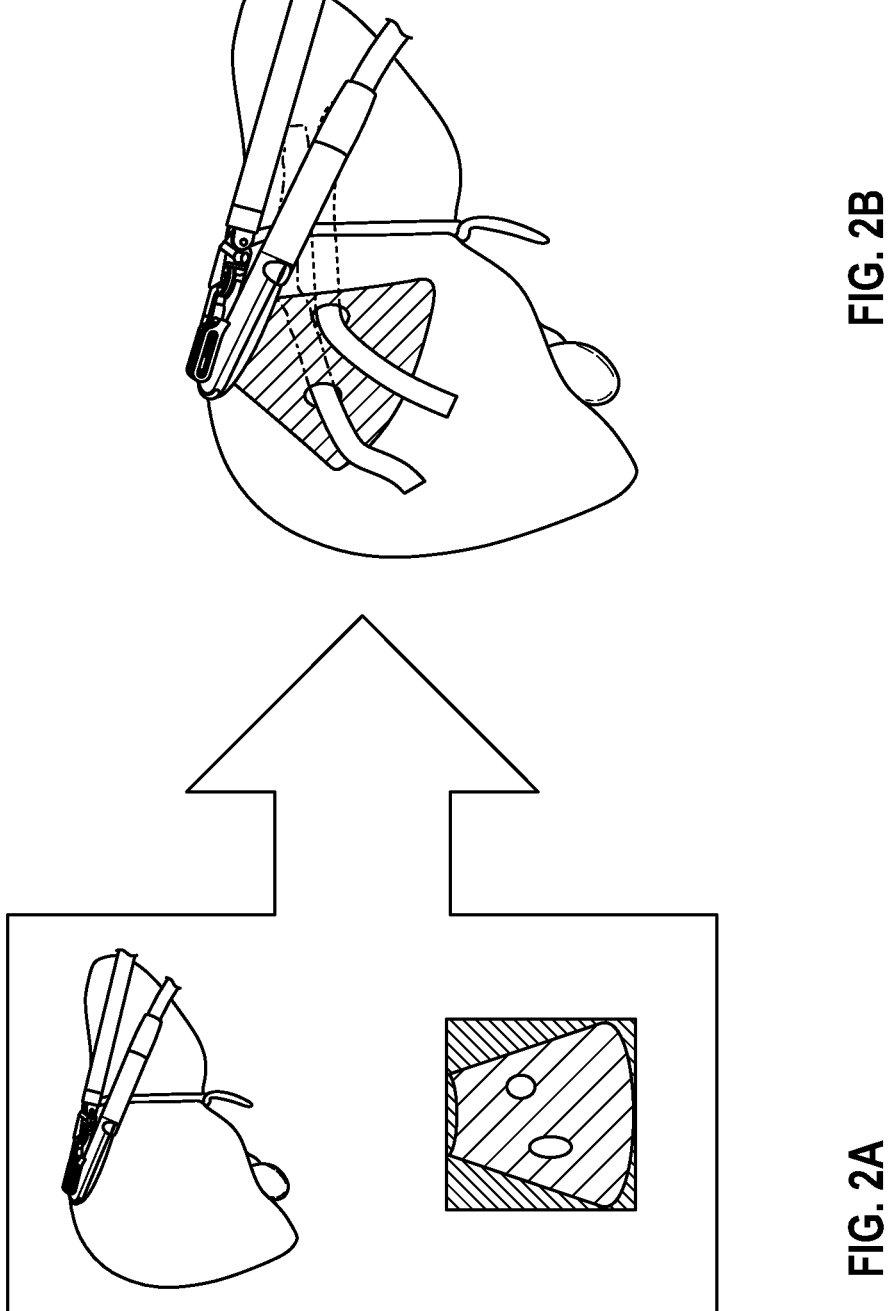
FIG. 2A illustrates a real-time image of a laparoscopic instrument including an imaging device within a surgical site.
FIG. 2B illustrates a real-time image of the laparoscopic instrument of FIG. 2A with a superimposed computer-generated image of patient anatomy derived from the ultrasonic image.
Figure 3:
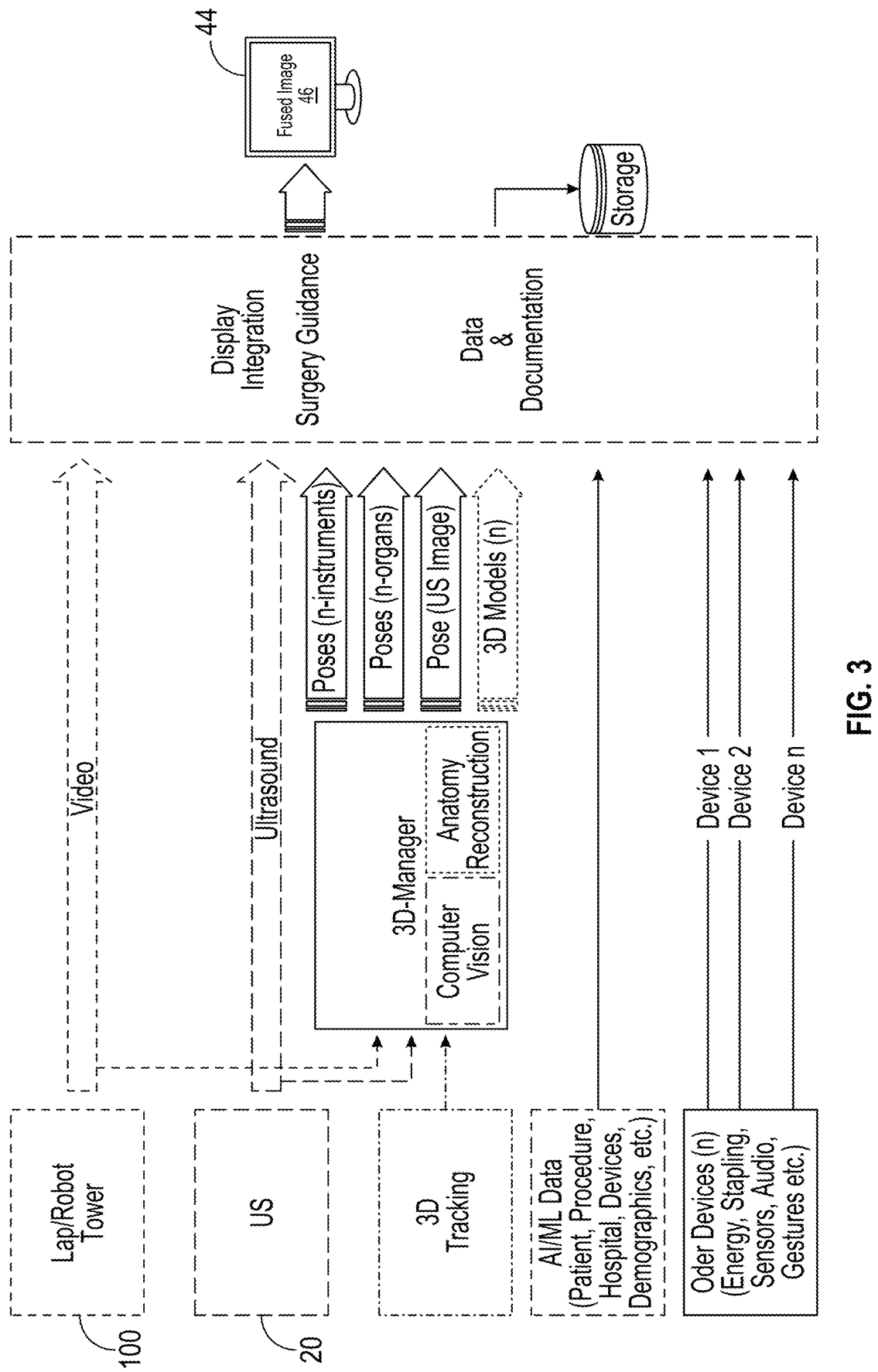
FIG. 3 is a schematic configuration of a visualization or imaging system in accordance with an embodiment of the disclosure.

With reference to FIGS. 2A, 2B, and 3, in aspects of the disclosure, enhanced visualization and image fusion is provided, whereby the system 1 takes image streams from a laparoscopic or robot tower 100 (white-light cameras) and an ultrasound probe 20 as inputs. Based on the spatial position of the ultrasound probe 20 inside the view of camera 16 (FIG. 1), the system 1 calculates the appropriate projection in 3D of the 2D ultrasound image, and fuses it together with the laparoscopic view for display on display 44 (FIG. 1). In aspects, the real-time image of the laparo-scopic instrument may be transformed to reflect the relative 6-axis pose. As depicted in FIG. 3, display 44 renders a fused image 46 comprising the laparoscopic video image with the projected ultrasound image calculated as described above.

With reference to FIGS. 2A and 2B, the system 1 guides the user or autonomously controlled robot to ultrasonically scan a volume of tissue that may be segmented by edge finding or machine learning methods to visualize the patient anatomy within the scan volume. The ultrasound segmentation is near real-time, enabling the system to control ultrasound modalities to automatically aid in structure segmentation, b-mode doppler, or elastography. The system 1 conveys the speed and direction of scanning to the user for manual movement of the ultrasound probe 20 or to the robot interface for autonomous scanning of the patient anatomy. The surgeon need not be an expert in orienting a ultrasound probe or interpreting the image as the system addresses these needs. The autonomous function of the ultrasound may be further guided by the preoperative imaging CT, MRI or the like providing additional cues to ultrasound movement and mode in order to best segment relevant structures and ultimately all image modalities.

The system 1 may be configured to process, in real-time, the incoming ultrasonic imaging to generate anatomy reconstructed models. The reconstruction routines combine conventional and AI methods to process the incoming ultrasound and the camera imaging. The process may also utilize a patient's pre-surgical imaging data. The reconstructed models are rotated/translated/scaled according to the position of the ultrasonic-probe 20 relative to the camera 16, and merged to generate the visual output. Different combinations of opacity levels, wireframe representation, colors, etc. can be used to highlight different structures at different times.

The system 1 is configured to implement real-time identification of anatomical and critical structures and/or tissue planes and dynamic tracking. This feature, combined with procedure-specific surgical planning parameters, allows the system 1 to identify the safest and most efficient path for surgical instruments and camera position. The system 1 conveys this information to the clinician using visual and/or audible cues including suggesting procedure steps and the instrument's path. In the case of robotic or actuated instruments, the system 1 can also drive such instruments/tools 22 and/or the camera 16.

In aspects, to identify and display critical structures of tissue (e.g., arteries), the camera 16 may include an infrared transmitter, such as, for example, infrared light-emitting diodes ("IR-LEDs") or lasers for transmitting near-infrared light, and one or more infrared receivers or sensors for receiving near-infrared light. The combined infrared transmitter and receiver is configured to detect the critical structures within the imaged tissue. The infrared transmitters and receivers are in communication with the processing unit 30 (FIG. 1) for generating a digital image of vasculature targeted by the infrared transmitters. The processing unit 30 is in communication with the infrared transmitters and receivers. As such, the amount of infrared light transmitted to tissue by the infrared transmitters and the amount of infrared light received by the infrared receivers is known by the processing unit 30. The processing unit 30 is configured to use this data to generate a digital image of the vasculature targeted by the infrared transmitters and display or super-impose the digital image of the vasculature over the real-time image of the surgical site, as shown in FIG. 2B.

One or more surgical instruments of the surgical system 1 may be configured to be simultaneously tracked in 3D, using magnetic, optical, radar-based, inertial, or other suitable tracking systems, by attaching trackers or reference frames to the surgical instrument. Moreover, computer vision (either from single or stereo cameras), alone or in combination with one or more of these methods, may be used to track instruments and anatomy in 3D, usually relative to the camera coordinates system.

With reference to FIGS. 2A and 2B, image-Model 2D-to-3D mapping may be used to find the surgical instrument and anatomy poses relative to the camera. For example, given the intrinsics of the camera and two sets of corresponding 2D and 3D point (or shapes) coordinates, the system 1 calculates the transformation (e.g., three rotations and three translations) that describe the camera location when taking the 2D image of each tool (from image orthogonality and scaling), whose inverses describe the surgical instrument(s) transformations from the camera's origin.

Figure 4A:
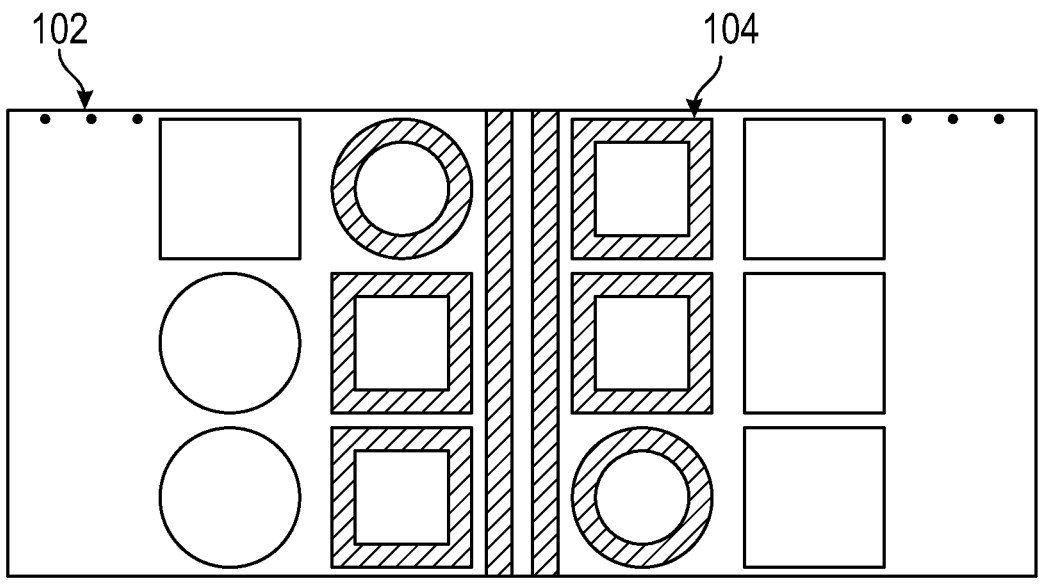
FIG. 4A is a plan view illustrating a label including a bar code to be wrapped about an ultrasonic probe.
Figure 4B:
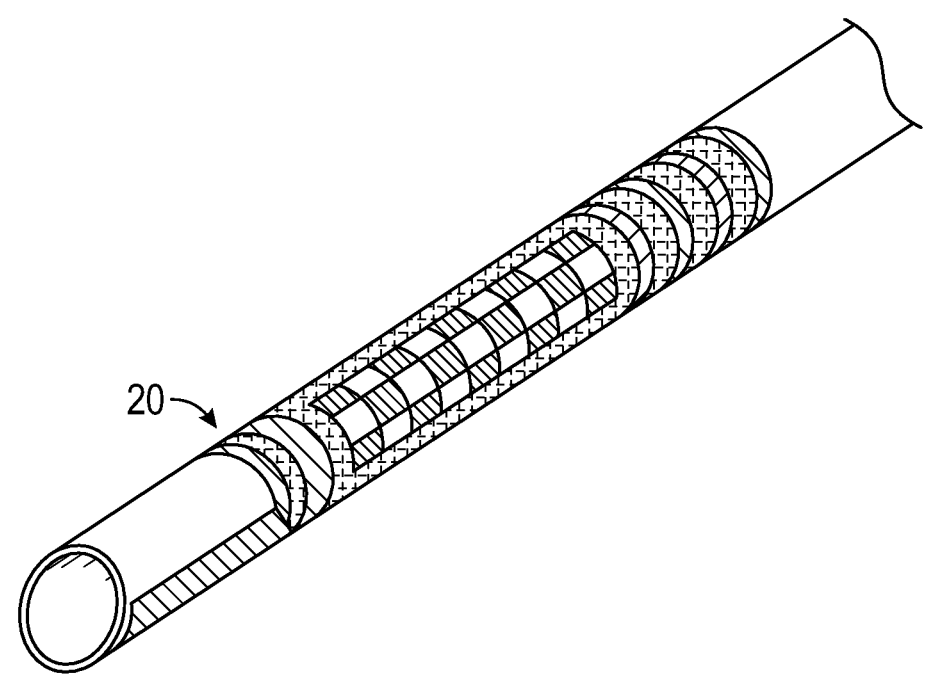
FIG. 4B is a perspective view illustrating a marking system wrapped about an ultrasonic probe to gain its 6-axis orientation.

Individual surgical instruments may be identified and tracked based on their shapes (e.g. using computer-automated model-fitting). Moreover, accuracy and performance of tracking and identification are complemented and improved by adding markings 102 (FIGS. 4A and 4B) to ease and advance automatic image processing, segmentation, and computer vision algorithms. For example, various strategically located markers can facilitate calculation of the 6 axis pose from the image corresponding to at least 4 non-coplanar points. Different color codes for fiducials can facilitate image processing by simplifying which component of the RGB channel is processed. Bar codes 104 on the label 102 may provide a fast way of identifying different tools, confirming model-fitting identification, as well as providing another well-defined target for 3D mapping. Color/shape coded rings can provide a fast way of identifying different tools, confirming model-fitting identification, as well as providing another well-defined target for 3D mapping. Checkerboard and other well-defined shapes/patterns can be used to correct for image distortion, as well as providing another well-defined target for 3D mapping. The label 102 may be wrapped on at least 3 sides of a round or square section of the ultrasound probe 20 for optical orientation and alignment.

One or more instruments of the surgical system 1 may be imprinted with or otherwise have attached thereto rulers or graduated grids to improve linear, surface, and volume estimates in the surgical field of view, either by placing the named grid directly adjacent to the structure to be measured, or used by the system 1 to dynamically adjust/fine-tune the computer vision features.

Referring to FIGS. 5A-11, the system 1 is configured to implement methods and techniques to improve anatomy tracking and computer vision by imprinting fiducials on organs' surfaces, such as, for example, ink marks and tattoos, burnt marks with energy devices, and/or imprinted patterns on film that covers anatomy. The system 1 maintains any combination of the anatomical image and the ultrasound image in the augmented surgical view by means of aligning it to the imprinted or natural organ fiducials. Maintaining this orientation provides the surgeon the opportunity to mark or initiate dissection of the organ or tissue without obstruction by the ultrasound image.

Figure 5B:
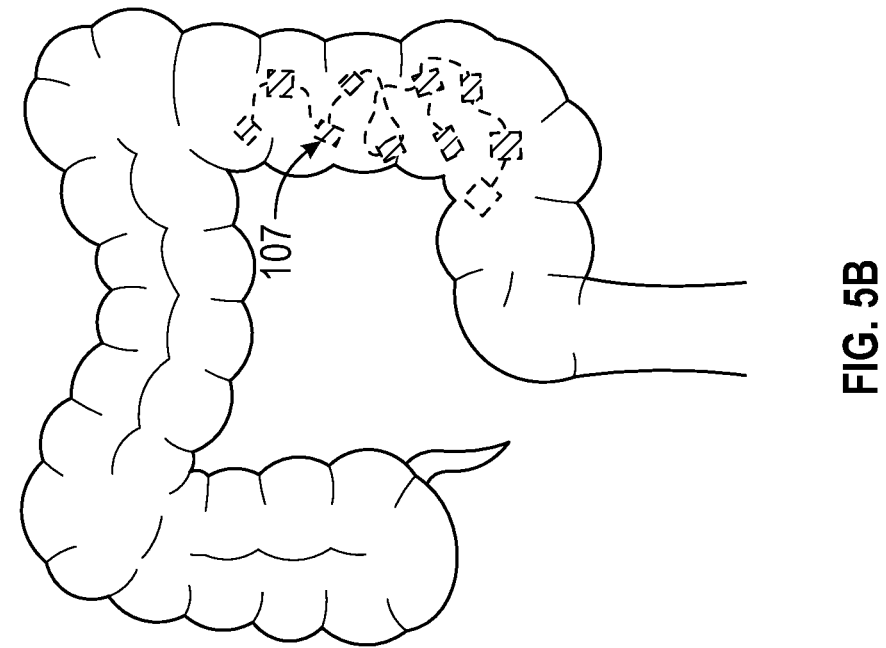
FIGS. 5A and 5B are schematic representations of a customized, battery-powered array of LEDs used as a fiducial marker.
Figure 5A:
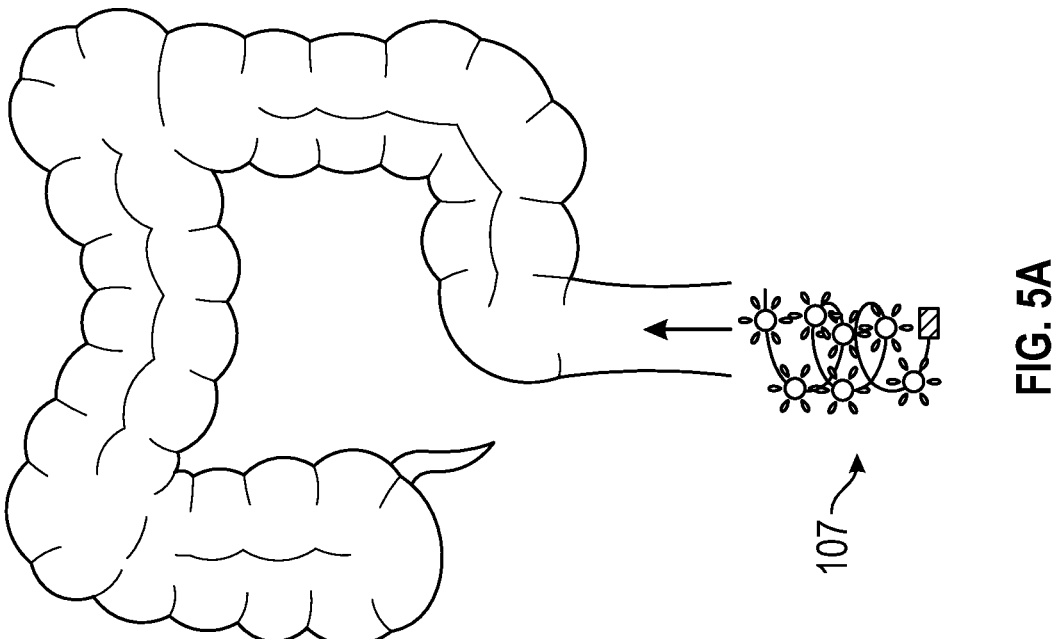
Figure 6:
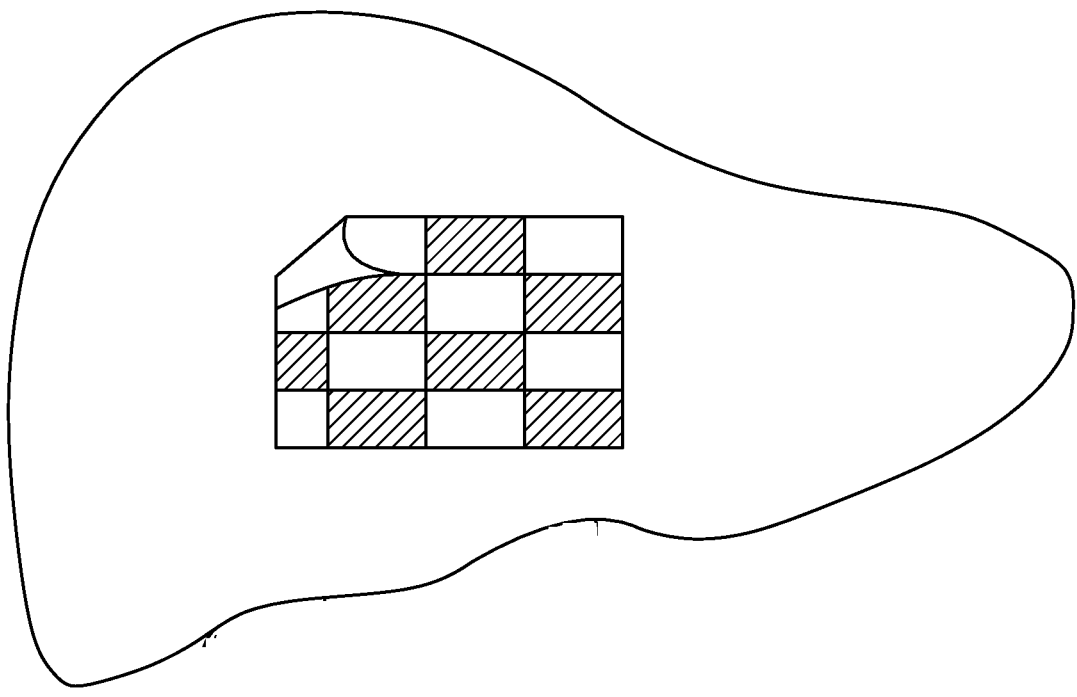
FIG. 6 is a schematic representation of a marking system adhered to a surface of an organ to optimize the performance of dynamic tracking and computer vision algorithms.
Figure 7A:
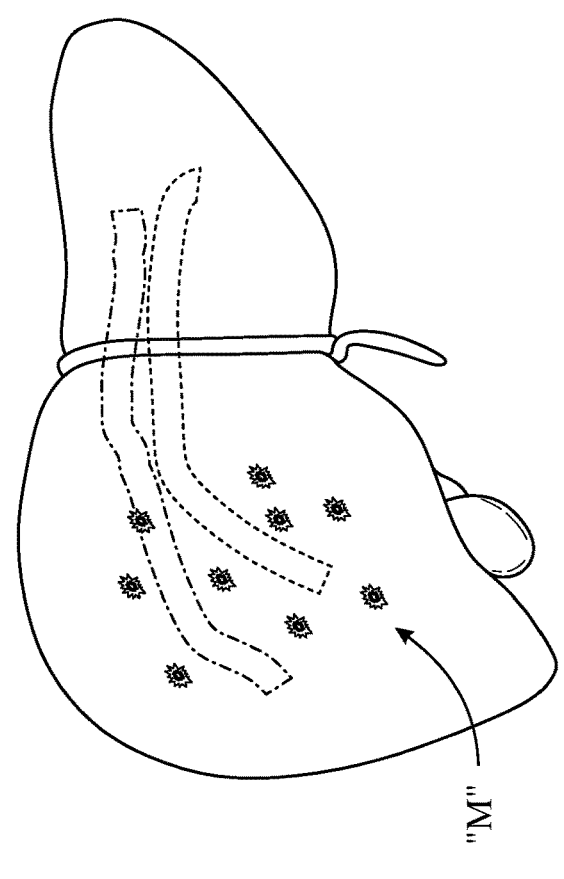
FIG. 7A illustrates an ultrasound probe scanning an organ with fiducial markers including a superimposed image of underlying tissue structures.
Figure 7B:
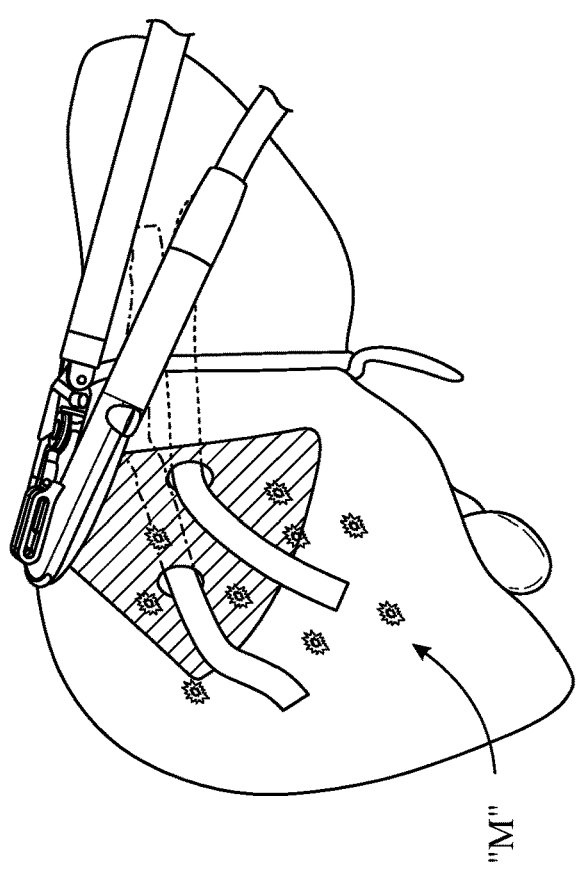
FIG. 7B illustrates the preservation of the organ of FIG. 7A and an ultrasonic image located relative to the organ or fiducials after the ultrasound probe is removed from the field of view.
Figure 8:
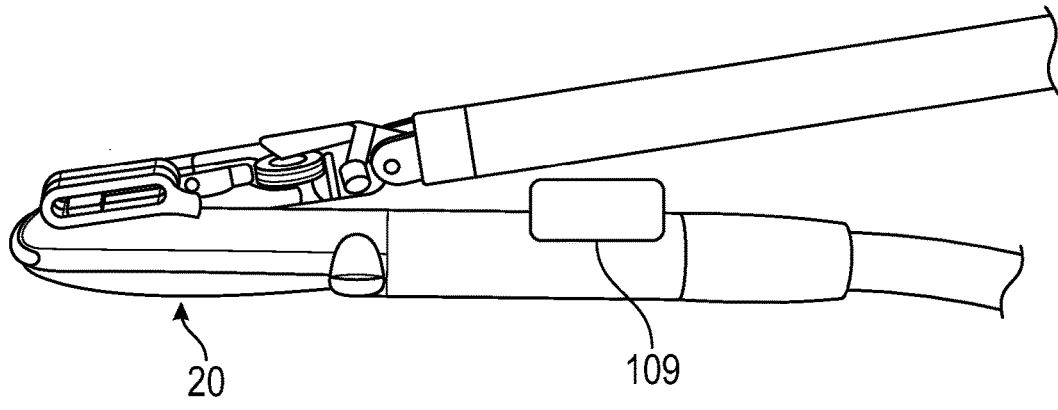
FIG. 8 illustrates an ultrasound probe with a multi-axis accelerometer-magnetometer-gyro augmenting orientation when the probe is out of the field or the marking system is obscured.

As shown in FIGS. 5A and 5B, a battery-powered array of LEDs 107 is used as a fiducial marker, wherein the array 107 is temporary introduced in the large intestine and the brightness of the LED's are captured by the laparoscopic or robotic camera through the intestine walls. The system 1 is further configured to implement methods and techniques to improve anatomy tracking and computer vision by placing fiducials and/or arrays inside hollow organs, as shown in FIGS. 5A and 5B, that can be perceived by the tracking sub-systems, such as, for example, magnetic markers, visible and/or NIR LEDs, dye (e.g. Indocyanine green), etc.

Computer vision-based tracking may be enhanced by combining a 9-axis (accelerometer+gyro+magnetometer) sensors 109 (FIG. 8) attached to the surgical instruments such as the ultrasound probe 20.

The system 1 integrates inputs from other devices to devices and surgical instruments, including energy devices generators, powered stapling units, voice commands, OR video, gestures, etc. The system 1 collects, processes, and records information about the procedure, the use of the surgical instruments and their performance, video streams, etc. The information is used to generate automatic procedure documentation, medical and technical reporting, and to retrofit data analytics tools.

Figure 9:
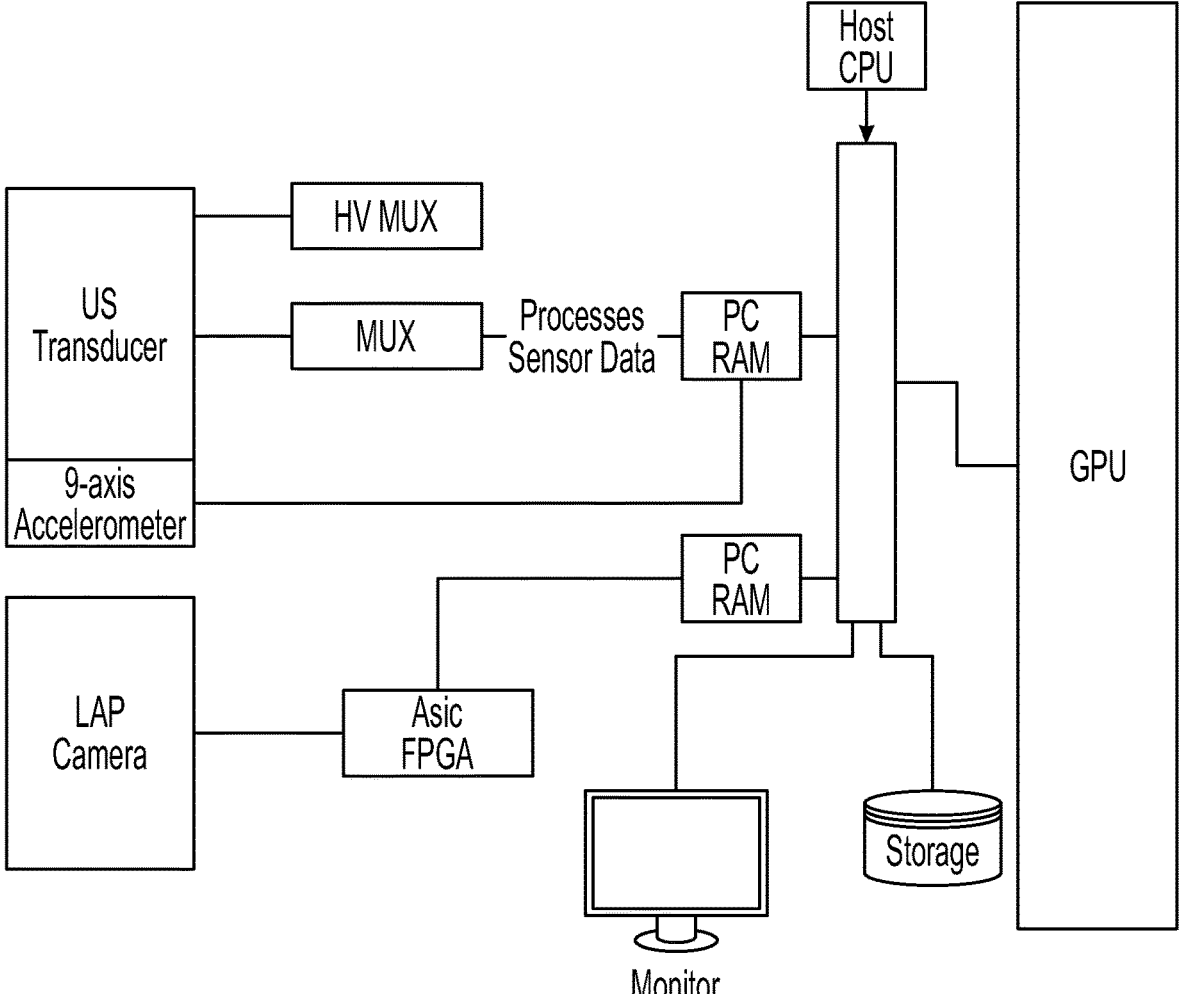
FIG. 9 is a schematic illustration of a combined GPU-based ultrasound and optical imaging system.

With reference to FIG. 9, another aspect of the disclosure is directed to a computer unit having the dual function of processing both ultrasound and optical images. By simultaneously processing both optics pipelines and ultrasound pipelines in a single GPU, the images are inherently better combined in real-time while the hospital system benefits by reduced hardware expense and clutter within the OR.

Figures 10, 11:
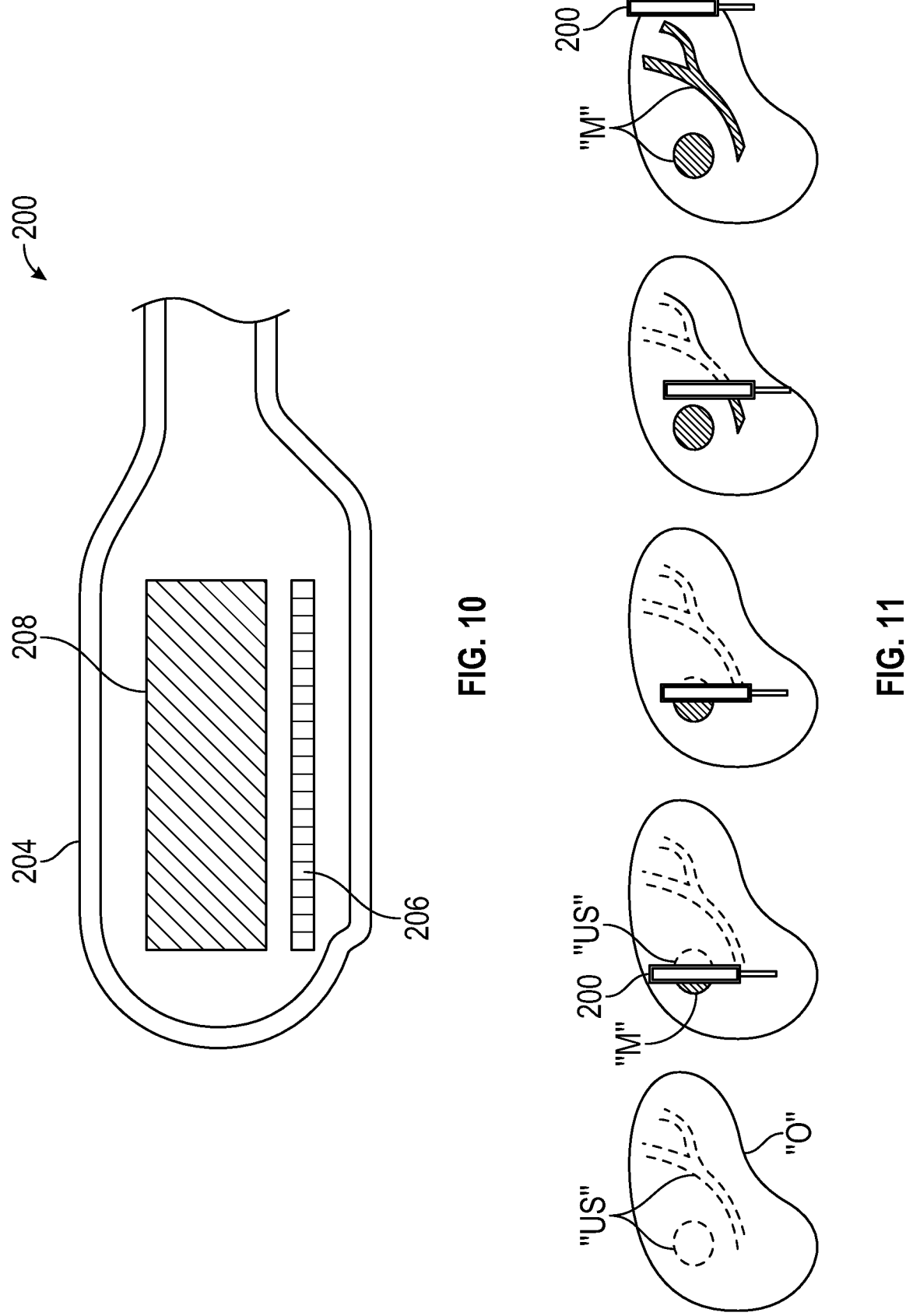
FIG. 10 is a longitudinal cross-sectional view illustrating an embodiment of a tissue-marking surgical instrument.
FIG. 11 is a schematic illustration of a series of operative steps involved in imaging and marking an organ utilizing the tissue-marking surgical instrument of FIG. 10.

With reference to FIGS. 10-11, a surgical instrument 200, such as, for example, a tissue-marking device is provided. The surgical instrument 200 is configured to both identify underlying structures "US" of an organ "0" (e.g., those structures not visible on the organ's surface) and imprinting fiducials or markings "M" on the organ's surface, such as, for example, ink marks and tattoos, burn marks and/or imprint patterns on a film that covers the organ surface, to make it easier for the clinician to make an incision while avoiding cutting into a tumor, vessel, or other underlying structure.

The surgical instrument 200 includes an end effector having an outer housing portion 204, a marking element, such as, for example, a printing array 206 supported in the outer housing portion 204, and an image sensor assembly 208 supported in the outer housing portion 204. The printing array 206 include a plurality of electrodes or other suitable heating elements configured to burn or otherwise mark the organ surface. In aspects, the printing array 206 may include a dye or ink-applicator, a laser printer, or other suitable tissue-marking element or elements. The printing array 206 may be disposed adjacent an opening in a bottom surface of the outer housing portion 204 and beneath the image sensor assembly 208. The printing array 206 may be configured to mark the organ surface with different patterns (e.g., dotted lines, symbols, etc.) and colors (in the case of ink) to differentiate structures from one another.

The image sensor assembly 208 may be an ultrasound transducer, an acoustic lens, or the like. The image sensor assembly 208 is configured to image the organ and transmit the images to a processor, which identifies the underlying structures "US" within the organ "O." As shown in FIG. 11, the processor may automatically actuate the printing array 206 to mark the organ surface at those locations above the identified critical structures "US" as the surgical instrument 200 is moved across the organ surface. In some aspects, instead of the processor automatically actuating the printer array 206, a clinician may selectively actuate the printer array 206. In aspects, the image sensor assembly 208 may be configured to send the images to a display for viewing by a clinician. The clinician may then mark the organ surface based on the images of the critical structures on the display. It is contemplated that the depth at which the critical structure is located relative to the organ surface may be measured and marked onto the organ surface.

The term "image" as used herein may include still images or moving images (for example, video).

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Python, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A method for preparing a surgical site for a surgical procedure, comprising:
    receiving, at a computer unit, an ultrasound image of an organ from an ultrasound probe;
    receiving, at the computer unit, a video image of a surface of the organ from a laparoscopic camera;
    detecting, in the video image acquired by the laparoscopic camera, at least four non-coplanar optical fiducial markings disposed on a curved outer surface of the ultrasound probe and configured to enable three-dimensional pose determination of the ultrasound probe, and calculating, from the detected fiducial markings, a six-degree-of-freedom pose of the ultrasound probe relative to the laparoscopic camera;
    calculating a projection of the ultrasound image within the video image acquired by the laparoscopic camera, based on the six-degree-of-freedom pose of the ultrasound probe;
    fusing the ultrasound image with the video image and displaying the fused image on a display device;
    identifying a critical structure beneath the surface of the organ based on the ultrasound image;
    marking the surface of the organ at a location overlapping with the identified critical structure and placing, on the surface of the organ at that location, a temporary fiducial mark that is visible in the video image; and
    removing the ultrasound probe from the field of view of the laparoscopic camera and maintaining display of the fused image with reference to the temporary fiducial mark visible in the video image.

2. The method according to claim 1, wherein the surface of the organ is marked with the ultrasound probe.

3. The method according to claim 1, wherein marking the surface of the organ includes marking the surface of the organ with a mark having a shape and size that approximates a shape and size of the identified critical structure.

4. The method according to claim 1, wherein the critical structure includes at least one of a tumor or a blood vessel.

5. The method according to claim 1, wherein marking the surface of the organ includes applying energy to the surface of the organ sufficient to burn the surface of the organ.

6. The method according to claim 1, wherein marking the surface of the organ includes applying an ink, dye, or chemical agent to the surface of the organ.

7. The method according to claim 1, further comprising:

displaying, in real-time, the received video image of the surface of the organ; and superimposing an augmented image of the critical structure over the displayed video image of the surface of the organ.

8. A surgical system, comprising:

a laparoscopic camera configured to acquire a video image of an organ;

a surgical instrument including an ultrasound transducer configured to locate and generate an image of an underlying structure within the organ; and a computer unit configured to:

detect, in the video image acquired by the laparoscopic camera, at least four non-coplanar optical fiducial markings disposed on a curved outer surface of the surgical instrument and configured to enable three-dimensional pose determination of the ultrasound transducer, and calculate, from the detected fiducial markings, a six-degree-of-freedom pose of the ultrasound transducer relative to the laparoscopic camera;

display, in real-time, the video image of the organ on a display device;

based on the calculated six-degree-of-freedom pose of the ultrasound transducer relative to the laparoscopic camera, augment the displayed video image of the organ by superimposing the image of the underlying structure within the video image acquired by the laparoscopic camera;

place, at a location overlapping the underlying structure, a temporary fiducial mark on a surface of the organ that is visible in the video image; and maintain display of the augmented video image after the ultrasound transducer is removed from a field of view of the laparoscopic camera with reference to the temporary fiducial mark visible in the video image.

9. The surgical system according to claim 8, wherein the surgical instrument includes:

a marking element configured to mark the surface of the organ.

10. The surgical system according to claim 9, wherein the marking element includes at least one heating element configured to apply energy to the surface of the organ.

11. The surgical system according to claim 9, wherein the marking element includes an applicator configured to apply at least one of a dye, ink, or chemical agent to the surface of the organ.

12. The surgical system according to claim 9, further comprising a processor in communication with the marking element and the ultrasound transducer, wherein the processor is configured to automatically actuate the marking element to mark the surface of the organ upon the ultrasound transducer locating the underlying structure.

\* \* \* \* \*